(12) United States Patent
Varghai et al.

(10) Patent No.: US 10,617,432 B2
(45) Date of Patent: Apr. 14, 2020

(54) CARTILAGE HARVESTING UNIT

(71) Applicant: CO-AX Technology, Inc., Solon, OH (US)

(72) Inventors: Davood Varghai, Beachwood, OH (US); Bahman Guyuron, Lyndhurst, OH (US)

(*) Notice: Subject to any disclaimer, the term of this patent is extended or adjusted under 35 U.S.C. 154(b) by 369 days.

(21) Appl. No.: 15/416,086

(22) Filed: Jan. 26, 2017

(65) Prior Publication Data
US 2018/0206858 A1    Jul. 26, 2018

(51) Int. Cl.
*A61B 17/16* (2006.01)
*A61B 17/00* (2006.01)

(52) U.S. Cl.
CPC ...... *A61B 17/1635* (2013.01); *A61B 17/1615* (2013.01); *A61B 2017/00792* (2013.01); *A61B 2017/00969* (2013.01); *A61B 2217/005* (2013.01)

(58) Field of Classification Search
CPC .................................................. A61B 17/1635
See application file for complete search history.

(56) References Cited

U.S. PATENT DOCUMENTS 8,034,003 B2 * 10/2011 Pesce ................... A61B 10/025
600/562

\* cited by examiner

*Primary Examiner* — Nicholas W Woodall
(74) *Attorney, Agent, or Firm* — Cooper Legal Group, LLC

(57) ABSTRACT

Systems and methods that enable harvesting of cartilage from a subject (e.g., a patient) via a harvesting unit that mitigates or eliminates a requirement of dicing and/or separation/division of the cartilage by hand. The harvesting unit employs a power supply to accumulate and cut the cartilage. By employing the harvesting unit, an automatic accumulation and reduction of size for the cartilage is provided, while freeing a person from having to manually dice the cartilage.

12 Claims, 12 Drawing Sheets

CARTILAGE HARVESTING UNIT

BACKGROUND

In general, reconstructing of depressions or deficiencies in a rigid framework for reconstructive treatment of a patient can typically require insertion of a firm filling. Such filling can itself use autogenous living materials in form of grafts including bone, fascia, cartilage, dermis and fat, for example. Moreover, throughout history of cosmetic treatments, other non-living materials of humans such as boiled bone, ivory, preserved cartilage, gutta-percha, and preserved fascia, have also been employed as part of such filling. Typically from such list, cartilage has generally emerged as a preferred material that constitutes such filling, in modern cosmetology fields.

Commonly, the cartilage can be introduced as a carved block or mass of sliced or diced particles. Typically the term diced may refer to small segments that are cut in form of a flat shaving. For example, this can include cube segments without having sharp edges such as cartilage being manually chopped into multi-faceted particles, generally about 1 to 3 mm in diameter.

To this end, cartilage grafting has been used extensively to correct both functional and aesthetic aspects of nasal frameworks in patients, via replacing layered septal grafts, stacked conchal grafts, and carved costal cartilage grafts, for example. Stated differently, both reconstructive and cosmetic surgeries—which are among the most frequently performed procedures especially in craniofacial surgeries today—routinely employ cartilage grafts.

As such, cartilage grafting can be performed in plate or diced forms, for example. Advantageously, diced grafting may require relatively smaller incisions hence reducing patient-recovery-time; which remains in contrast to plate grafting that requires substantially larger incisions. Stated differently, when a full-thickness cartilage or solid graft is employed instead of diced grafting, a splinting the chest wall of a patient can be required, which in turn can potentially cause atelectasis and other pulmonary complications for the patient—hence mandating rigorous medical attention during the immediate postoperative period.

On the other hand, employing a substantially small incision(s) and avoiding full-thickness harvest can typically mitigate such adverse effects. To this end, diced cartilage grafts are typically deemed a valuable addition is reconstructive and cosmetic surgeries.

Moreover, such diced cartilage grafts are considered highly flexible, when correcting aesthetic & functional aspects of patients. For example, their use can simplify various challenges in all of rhinoplasty—dorsal augmentation—whereby complications have remained relatively manageable and their correction simple to administer.

Notwithstanding, the whole process of manually dicing cartilage as in conventional systems, is typically deemed time consuming—which in itself can further prolong operation procedures. For example, lack of agility in conventional procedures of cartilage dicing can further prolong anesthesia and its associated costs for the patients.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

Various aspects of the subject disclosure provide for a hand-held harvesting unit that accumulates and stores cartilage (e.g., from body of a patient or subject), for a subsequent use or processing thereof. According to one aspect, the harvesting unit can comprise a scooper component and a cutter component, wherein the scooper component can acquire or accumulate the cartilage; and the cutter component can subsequently divide such cartilage into a plurality of additional pieces, for a size-reduction of the cartilage. To this end, the subject disclosure mitigates or eliminates a requirement of dicing the cartilage and/or a separation/division of the cartilage by hand (e.g., manually)—as performed in conventional procedures, for example.

In this regard, the scooper component can substantially function as a collecting mechanism that gathers cartilage from the patient (e.g., by direct contact with the patient's body tissues) for subsequent processing—as opposed to—merely shaping such cartilage on body of the patient, to fashion a specific configuration. Furthermore, partitioning of the cartilage and its division for size reduction by the cutter component of the subject disclosure, frees a person from having to manually dice the cartilage. Hence, the harvesting unit enables an automatic reduction of size for the cartilage that is collected—hence, improving upon To this end, the harvesting unit can facilitate consistency of procedures and improve efficiency, when collecting and storing chondrocyte cells and their related extracellular matrix—for subsequent use (e.g., cartilage regeneration, creating cartilage dough for surgical procedures, cartilage injection, and the like). For example, such can facilitate employing injectable cartilage with a needle(s) or substantially small caliber cannula to mitigate conventional surgery and correct deformities or the facial imperfections with typically minimally invasive procedure in an office setting with shorter recovery time than conventional surgical procedures.

According to a further aspect, the harvesting unit can comprise a scooper component, or a cutter component, or a combination thereof, wherein the scooper component can acquire the cartilage (e.g., by peeling or shaving directly from body of a live or dead subject); and the cutter component can subsequently slice, dice, or grind the cartilage based on predetermined criteria.

Such predetermined criteria can relate to characteristics for extracellular matrix of the cartilage and based on subsequent processing requirements thereof, such as, dimensions, rate for division of chondrocyte cells, compressive or tensile strength, shear loading, viscoelastic properties, frictional characteristics, diffusion properties, and the like. It is to be appreciated that each of the scooper component or the cutter component, can itself include additional scooper elements (or cutter elements), which further facilitate various staged operations corresponding to the scooper component (or the cutter component).

In a related aspect, the scooper component can induce an amount of predetermined energy on cartilage of a patient or subject that is sufficient to remove cartilage from body of the patient or subject, and intake the cartilage into the harvesting unit. To this end, the amount of energy induced by the scooper component onto the cartilage can be adjusted by factors such as hardness of the scooper component, speed of operation, grip force of the operator, and the like—to reach a predetermined threshold that is sufficient for removal of the cartilage from the subject and into the harvesting unit.

It is to be appreciated that even though the subject disclosure primarily describes operation of the scooper component in conjunction with a shaver component that rotates (see infra), the subject patent application is not so limited and other mechanism for inducing energy on the cartilage for a separation thereof from body of the patient or subject, are well within the realm of the subject innovation. For example, the scooper component can employ any type of energy inducing mechanism on the cartilage such as; punching; piercing; drilling; lateral cutting, chipping, employing source of energy like laser, and the like, or a combination thereof; when gathering or accumulating the cartilage from body of the subject and an intake thereof into the harvesting unit.

In a related aspect of the subject disclosure, the scooper component can further include a shaver component having a plurality of protrusions that engage with the cartilage for a peeling/shaving and an accumulation thereof. The plurality of protrusions associated with the shaver component, can represent multiple semi-conical shaped blades that are raised over a curved surface and can shave cartilage in form of stripes via a rotating motion of the shaver component. For example, the shaver component can employ a symmetrical configuration, to facilitate its handling by an operator (e.g., facilitating operation of the scooper component at different hand-tilt-angles when contacting cartilage of the patient or subject.)

To this end, the harvesting unit of the subject disclosure can initially harvest and subsequently supply the cartilage for subsequent procedures. Such subsequent procedures can pertain to injecting the cartilage with a needle or substantially small caliber cannula (e.g., treating/correcting deformities such as facial imperfections with reduced invasive procedures in an office setting.) Accordingly, the subject disclosure describes an automated process for preparing/creating cartilage and reducing a size thereof, which mitigates or eliminates a requirement for manually dicing the cartilage by hand, for example.

Such reduction in size can be based on predetermined criterion, such as requirements for cartilage injection, which can depend on how the cartilage can be subsequently used (e.g., in reconstructive operations.) Moreover, the scooper component can be operatively connected to an electromotor, such as an electric brushless motor that employs permanent magnets (e.g., that rotate around a fixed armature). Such electromotor can supply a substantially high torque to weight ratio to the shaver component, which in one particular is included as part of the scooper component, for example.

Accordingly, the harvesting unit can mitigate various risks associated with patient treatment; by facilitating production of diced cartilage in an automatic manner (e.g., by using a power source for cartilage dicing and/or eliminating preparing cartilage by hand.) To this end, the harvesting unit of the subject innovation accumulates cartilage and subsequently supplies it in a manner that readily encourages or facilitates employing diced or grinded cartilage for medical procedures.

In one particular aspect, the harvesting unit can be in form a disposable unit that can be discarded upon being used on the patient. For example in such disposable harvesting unit, pressing a button can release a piston element that breaks-up the disposable unit, to expose the cartilage accumulated therein. Such facilitates removing the cartilage accumulated for subsequent usage.

According to a further aspect, the scooper component can shave cartilage in form of a stripe configuration (e.g., cartilage in shape of a band having a width of 0.2 mm-0.4 mm, and a length of 1 mm-3 mm). Such cartilage in form of a stripe configuration can subsequently be diced into pieces (e.g., having a width of 0.2 mm-0.4 mm, and a length of 0.2 mm-0.4 mm). It is to be appreciated that such ranges are exemplary in nature and other dimensions can be obtained by varying a size of the shaver component and associated cross cutter. For example, additional grinding stages can be employed that can further grind the cartilage into a dough having a particle size of 0.05 mm-0.1 mm diameter, whereby such particles can pass through 18-16 gauges for purpose of cartilage injection.

In a related aspect, the harvesting unit can further employ a vacuum chamber that supplies a suction mechanism that intakes the cartilage into the harvesting unit, via a differential pressure during operation. Such suction mechanism can further be facilitated in a scenario wherein the scooper component employs a shaver component having rotational movement when accumulating the cartilage from the subject; whereby such rotational movement of the shaver component further increases the differential pressure between the vacuum chamber relative to other parts of the harvesting unit.

In accordance with a methodology of the subject innovation, an automated process for dicing the cartilage is disclosed (e.g., that mitigates or eliminates a requirement for manually dicing the cartilage by hand.) Initially the harvesting unit can receive direct contact from the cartilage of the subject such as the patient's body tissues. Upon the harvesting unit contacting the subject, an amount of energy can be induced from the harvesting unit upon the subject.

Such amount of energy is sufficient to separate the cartilage from the subject and can be a function of various operations and characteristics of the harvesting unit, such as speed, power, material characteristics (e.g., hardness of the scooper component) and the like. Upon exertion of such energy onto the cartilage, the cartilage can be accumulated and taken into the harvesting unit—such as by shaving the cartilage via the scooper component. Subsequently, the cartilage can be drawn into (e.g., sucked into) the harvesting unit and accumulated therein. The cartilage can then be broken into a plurality of pieces, via one or more slicing or dicing or grinding components.

According to a further methodology of the subject innovation, the cartilage can initially be shaved via a shaving component, which facilitates removing cartilage from the subject and accumulate it for subsequent use. By employing a differential pressure, such cartilage can then be drawn into the harvesting unit. Next, the cartilage can be stored in the harvesting unit for a subsequent processing thereof. For example, such subsequent processing can pertain to employing the cartilage that has been sliced or grinded for scientific and medical procedures such as: creating additional cartilage cellular structure; injecting into tissue of a patient that requires additional cartilage, and the like. In a related aspect, flow of the cartilage in the harvesting unit can further be facilitated by irrigating with phosphate buffered saline, normal saline or employing various isotonic or non-isotonic solution, which can adjust the viscosity of flow that is associated with movement of the cartilage within the harvesting unit.

In a related aspect according to the subject innovation, a pipe configuration can convey the cartilage into the vacuum chamber. It is to be appreciated that before entering the vacuum chamber, such cartilage can be in form of a stripe, or further divided into diced segments or further fragmented into dough, based on the number of cutting or slicing processes performed thereon. For example, initially the scooper can accumulate the cartilage based on a shaving thereof from a patient to form stripes, wherein such stripes can further be diced based on a rotation of a cutter that further slices the cartilage en route to the vacuum chamber. Subsequently and within the vacuum chamber, the cartilage can be accumulated in a porous collecting chamber, whereby water an air is ejected from such porous collecting chamber, hence leaving the cartilage therein. Stated differently, the porous collecting chamber can function as a removably attachable/detachable cartridge(s) that contains the cartilage. For example, the vacuum chamber and the porous collecting chamber can be removable and disposable two shells chamber. Such collected cartilage can be of a size and density that when injected into imperfection spaces or volumes of the patient, can fill it up without substantially shrinking in due time, for example. In effect, the cartilage collected by the harvesting unit includes a matrix of cells that have not been substantially damaged by the slicing, grinding and cutting operation. Hence, the cartilage is not subsequently absorbed by the patient body. As such, the cartilage collected by the harvesting unit, contains substantially live cells after being sliced and diced—wherein cells associated with the cartilage are not substantially affected by the separation/division operations performed by the harvesting unit. For example, by substantially minimizing a surface contact area between the cartilage and cutting elements, bursts for live cells of the cartilage can be mitigated.

In a related aspect, the user (e.g., a surgeon) can dynamically (such as on-the-fly and while employing the harvesting unit) change the size of cartilage stripes that are being accumulated into the harvesting unit, by adjusting size of the orifices positioned on the shaver component associated with the scooper component. For example, an inner shell membrane can be positioned underneath the scooper component (e.g., covered thereby), such that a swivel motion of the inner shell membrane relative to the scooper component can partially block an orifice size. A surface area of the orifice such blocked, can subsequently affect the size of cartilage stripes thus accumulated by the harvesting unit.

The following description and the annexed drawings set forth in detail certain illustrative aspects of the claimed subject matter. These aspects are indicative, however, of but a few of the various ways in which the principles of such matter may be employed and the claimed subject matter is intended to include all such aspects and their equivalents. Other advantages and novel features will become apparent from the following detailed description when considered in conjunction with the drawings. It is to be appreciated that the drawings are not necessarily to scale, and various components may have been represented out of proportion relative to other components, for example.

DETAILED DESCRIPTION

The various aspects of the subject innovation are now described with reference to the annexed drawings, wherein like numerals refer to like or corresponding elements throughout. It should be understood, however, that the drawings and detailed description relating thereto are not intended to limit the claimed subject matter to the particular form disclosed. Rather, the intention is to cover all modifications, equivalents and alternatives falling within the spirit and scope of the claimed subject matter.

Figure 1:
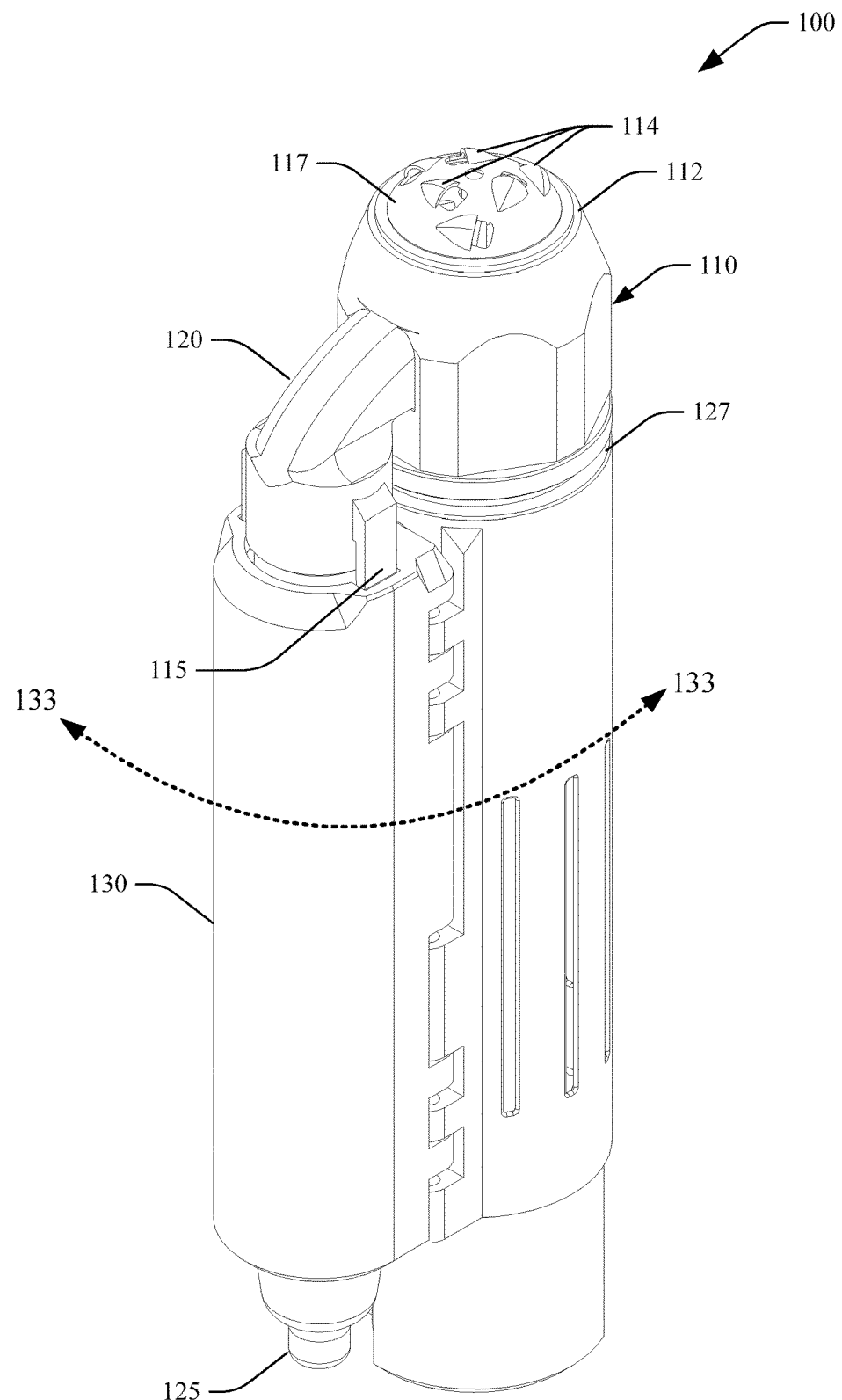
FIG. 1 illustrates a perspective of an exemplary harvesting unit that employs a vacuum chamber, in accordance with an aspect of the subject innovation.

FIG. 1 illustrates an exemplary perspective depiction of a harvesting unit 100 according to a particular aspect of the subject innovation. In one aspect, the harvesting unit 100 provides for an automated collection of cartilage for subsequent injection—as opposed to manually dicing the cartilage by a person to provide injectable cartilage, for example.

In general, cartilage represents a resilient-smooth-elastic-tissue, and rubber-like padding that can function as a cover; such as while protecting ends of the long bones at joints, for example. To this end, cartilage can characterize a structural component of the rib cage, the ear, the nose, the bronchial tubes, the intervertebral discs, and other body parts.

In addition, cartilage can further represent a valuable source of tissue for grafting in reconstructive treatment, as it can be readily available, bulky, easily shaped and survives well, for example. As such, cartilage remains non-dependent on blood supply (e.g., using Sulphur for its metabolism as opposed to oxygen from blood supply), and does not contain blood vessels (remaining avascular) or nerves (remaining aneural). Accordingly, nutrition can be supplied to its chondrocytes via diffusion.

In this regard, compression of the articular cartilage or flexion of the elastic cartilage generates fluid flow, which can further assist diffusion of nutrients to the chondrocytes. Compared to other connective tissues, cartilage generally has a slow turnover of its extracellular matrix and typically does not repair itself. Stated differently, cartilage exhibits limited repair capabilities—whereby because corresponding chondrocytes are bound in lacunae, they typically cannot migrate to damaged areas. To this end, cartilage damage can be difficult to heal, and because hyaline cartilage does not have a blood supply, the deposition of new matrix remains typically slow (e.g., damaged hyaline cartilage is usually replaced by fibrocartilage scar tissue.)

In one particular aspect, the automated collection of cartilage (e.g., without a dicing thereof by hand) via the harvesting unit 100 can facilitate increased consistency and improved efficiency, when collecting and storing chondrocyte cells and their related extracellular matrix. The cartilage thus harvested and accumulated by the harvesting unit 100 can subsequently be supplied for further processing of the cartilage, such as to facilitate surgical procedures on patients or subjects. For example, this can include employing the cartilage as filler material for treating or correcting deformities; mitigating imperfections, and the like, on a patient. Such further processing of the cartilage can include mitigating a requirement of invasive procedures on a patient, when supplying cartilage that is injectable in a patient body with a needle or substantially small caliber cannula.

As illustrated in FIG. 1, the harvesting unit 100 can further comprise a scooper component 110. As such, the scooper component 110 can acquire or accumulate the cartilage from a patient body when contacting it (e.g., a direct contact). In this regard, the scooper component 110 can further include a shaver component 112 that employs a plurality of protrusions 114, which can engage with a patient body tissues and its cartilage for an accumulation thereof. In one aspect, the protrusions 114 represent multiple semiconical shaped blades that are raised over a curved surface 117 and can shave cartilage in form of stripes, via a rotating motion of the shaver component 112.

It is to be appreciated that even though the subject application is primarily described in conjunction with a rotational movement of the shaver component 112—other mechanism are well within realm of the subject innovation. For example, the scooper component 110 can employ a lateral razor movement for peeling of the cartilage from body of a subject (e.g., a patient.) Likewise, a punching or piercing motion or employing a laser source can be employed when gathering or accumulating the cartilage from the subject, and for a subsequent processing thereof, for example.

Typically, the material employed in constructing the harvesting unit 100 can include any material approved by the Food and Drug Administration (FDA) for body contact, which further meets the working operation (e.g., mechanical requirements such as hardness, brittleness, energy transfer, induction, dissipation, and the like) when contacting body tissues of a patient. For example, the scooper component 110 and/or the shaver component 112 can be made from FDA approved metals (e.g., steel, aluminum, titanium, nickel, and the like) or composite materials (e.g., ceramic, plastics, carbon, and the like), whereby such FDA approved material are capable of inducing into cartilage of a patient or subject an amount of predetermined energy that is sufficient to remove the cartilage therefrom and into the harvesting unit 100.

The harvesting unit 100 can further employ a vacuum chamber 130, to maintain a differential pressure between the vacuum chamber 130 and its outside space or other parts of the harvesting unit 100. To this end, the vacuum chamber 130 can supply a suction mechanism that intakes the cartilage into the harvesting unit 100 via a differential pressure during operation. Such suction mechanism can further be intensified in a scenario, wherein the scooper component 110 employs a rotational movement via operation of the shaver component 112, when accumulating the cartilage from a patient or a live/dead subject (e.g., an animal). Hence, the rotational movement of shaver component 112 can reduce an air pressure on a side of the harvesting unit 100—as compared to—an air pressure on a side of cartilage on the body of the patient. Moreover, the vacuum chamber 130 can further employ a vacuum port 125 for enabling the vacuum operation thereof.

As further illustrated in FIG. 1, the harvesting unit 100 can further employ a pipe configuration 120 or vacuum tube that conveys the cartilage being shaved by the shaver component 112, into the vacuum chamber 130. Moreover, the harvesting unit 100 of FIG. 1 can employ a mechanical gasket elastomer 127 (e.g., an O-Ring) that can seat beneath the scooper component 110, to provide for a substantially tight-air seal in at the interface, for example. The mechanical gasket elastomer 127 can be made of material that adequately handles vibrations from the shaver component 112, while at the same meeting the requirements of pressure differences as required by the difference in pressure in the vacuum chamber 130 for sucking the cartilage into the harvesting unit 100.

The vacuum chamber 130 can further be operationally connected to a lock mechanism 115 that engages/disengages the vacuum chamber in to its position. For example, upon depressing the lock mechanism 115 the vacuum chamber 130 can become disengaged as to allow a swivel motion in direction 133 around a hinge, hence enabling an operator of the harvesting unit 100 to gain access to the cartilage accumulated therein. In one particular aspect, within the vacuum chamber 130 the cartilage can be accumulated in a porous collecting chamber (not shown), whereby water an air is ejected from such porous collecting chamber, and hence leaving the cartilage therein. Stated differently, the porous collecting chamber can function as a housing for removably attachable/detachable cartridges that contains the cartilage.

Figure 2:
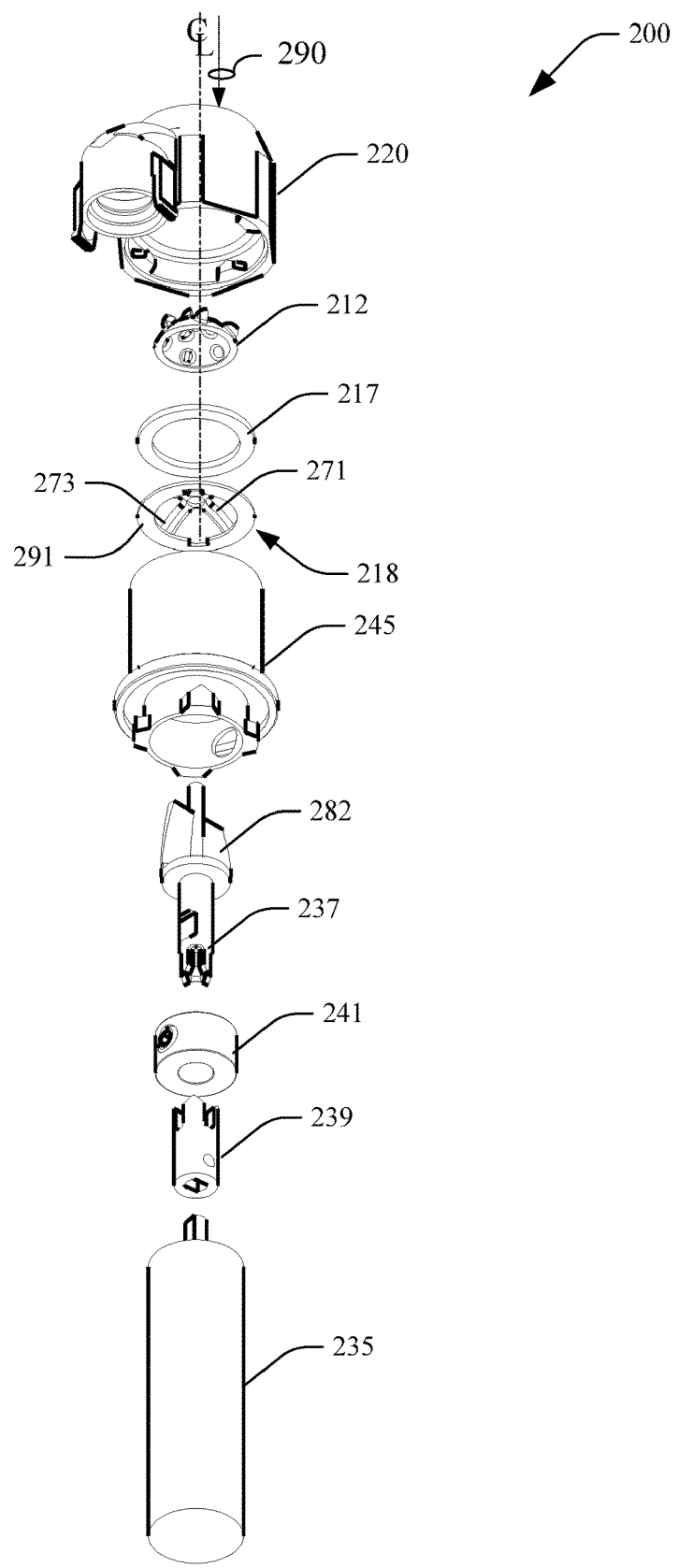
FIG. 2 illustrates a further perspective that identifies various parts for an exemplary harvesting unit having components that are being separated from each other, in accordance with an aspect of the subject innovation.

FIG. 2 illustrates a further perspective that shows various parts for an exemplary harvesting unit 200 having components that are depicted as being separated from each other. To further enhance the quality of FIG. 2, such exploded perspective is illustrated without depicting an outer shell of the harvesting unit 200. The shaver component 212—(that can be part of the scooper component 220)—is operationally connected to an electromotor 235 via a shaft 237 & coupling mechanism 239 and shaft locker 241, which can transfer a rotational movement and torque from the electromotor 235 to the shaver component 212. Moreover, the electromotor 235 can be in form of an electric brushless motor represented by a synchronous motor powered by a DC electric source (not shown), via an integrated inverter/switching power supply for driving the electric brushless motor 235 and an associated shaver component 212.

Additionally, the electromotor 235 can include permanent magnets that can rotate around a fixed armature (not shown), further eliminating problems associated with connecting current to the moving armature. The electromotor 235 can supply a substantially high torque to weight ratio, substantially high torque per watt (overall high efficiency), increased reliability, reduced noise, longer lifetime (no brush and commutator erosion as compared to brush motors), elimination of ionizing sparks from the commutator, and overall reduction of electromagnetic interference (EMI).

Figure 8:
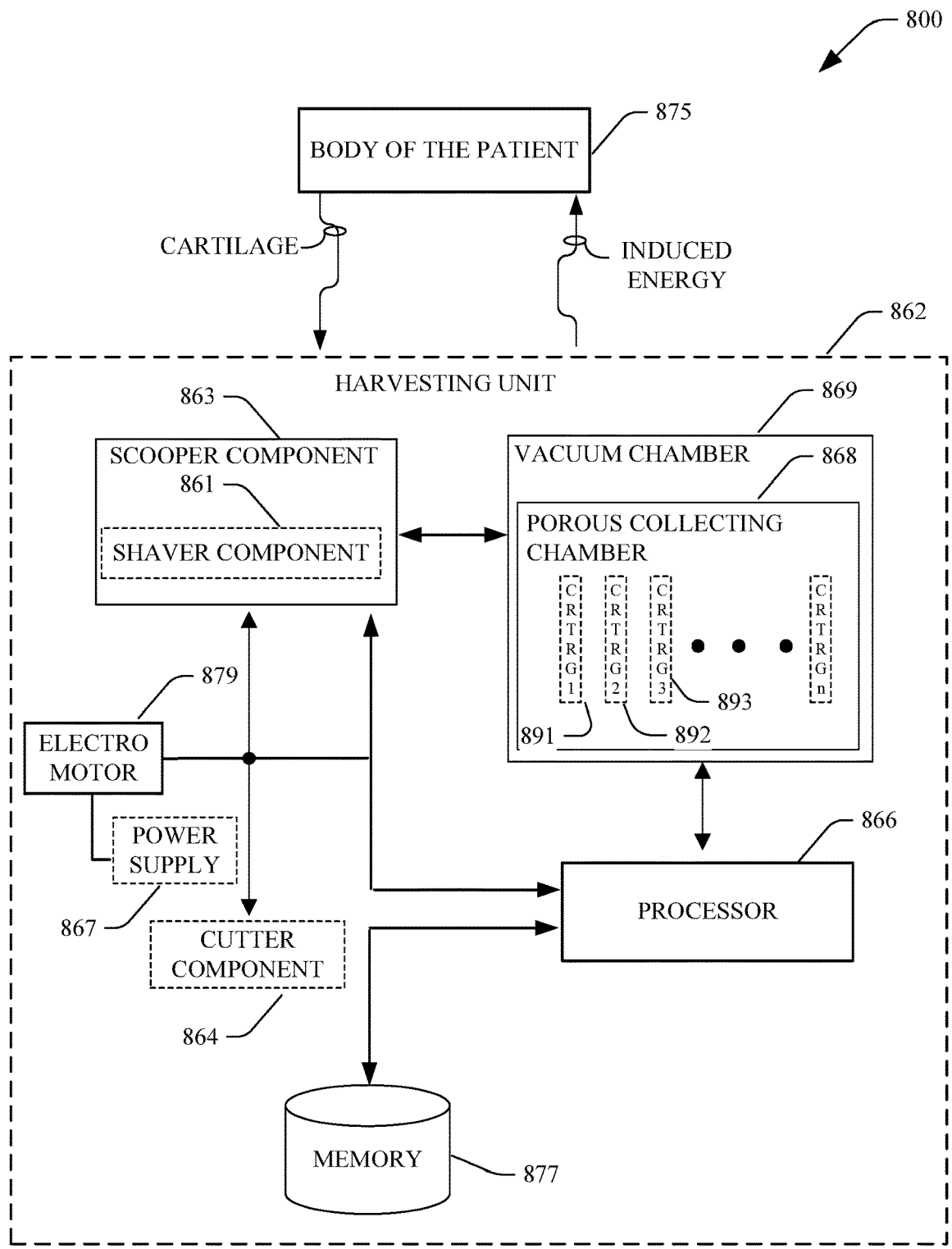
FIG. 8 illustrates a schematic block diagram of a harvesting unit according to an additional aspect of the subject innovation.

Moreover, the electromotor 235 can be implemented in a software environment that employs a microcontroller or microprocessor computer as described in detail with respect to FIG. 8 infra, and/or can be implemented in analogue hardware, or in digital firmware using a field-programmable gate array (FPGA). The electromotor 235 can supply a speed of rotation for the scooper component 220 within a range of between 500 to 2500 revolutions per second, for example. It is to be appreciated that other type of actuators that are associated with the electromotor 235 are well within the realm of the subject innovation. It is to be appreciated that the electromotor 235 can be associated with an ON/OFF control switch and/or a thermistor that exhibits a varied resistance, to vary the speed of rotation for the scooper component, for example.

As illustrated in FIG. 2, the scooper component 220 can acquire the cartilage via a shaver component 212. In this regard, the shaver component 212 can remove cartilage form body tissue of a patient, when it becomes in contact therewith. For example, the shaver component 212 can peel of cartilage form a patient body in form of a stripe configuration having a width within a range of 0.2 mm-0.4 mm. As illustrated in FIG. 2, the shaver component 212 is operatively connected to the electromotor 235, whereby a torque thereof affects an angular velocity of the shaver component 212.

The stripes of cartilage can subsequently pass, such as via a movement along a vertical center lines axis in direction of arrow 290 of the harvesting unit 200 and through a thrust bearing 217. Subsequently, the cartilage that has become in form of a stripe can be fed into the cutter component 218. As such, rotation of the shaving component 212 can be enabled, while at the same time the cutter component 218 can remain stationary. In one particular aspect, the cutter component 218 contains two curved blades 271, 273 that are connected to a circular frame 291. Accordingly, the cutter component can further dice the cartilage into smaller pieces that have a width within a range of 0.2 mm-0.4 mm.

It is to be appreciated that such ranges are exemplary in nature and other dimensions can be obtained by varying a size of the shaver component and/or a bit thereof, and the cross cutter operatively connected thereto. Moreover, the cartilage can further be divided into additional separate pieces on its way to being drawn into the vacuum chamber (not shown). For example, a grinder blade 282 that is positioned within a grinder shell grate 245 can further divide the cartilage into additional separate pieces, such as grinding the cartilage into dough that has a particle size within a range of 0.05 mm-0.1 mm diameter; whereby such particles can then employed for cartilage injection, (e.g., the cartilage being grinded is able to be passed through 18-16 gauge.)

Moreover, rotation of the grinder blade 282 can further facilitate movement of the cartilage into the grinder shell grate 245 itself (e.g., vacuum created by exertion of centrifugal forces and corresponding air movement from the grinder blade 282.) Hence, upon the cartilage exiting the grinder shell grate 245 and en route to the vacuum chamber (not shown), it can further engage with the rotating grinder blade 282, and consequently broken up to additional pieces thereby. It is to be appreciated that the above described dicing and grating procedures can be repeated by implementing additional cutters and graters, to obtain a predetermined size (e.g., from 0.001 mm to 0.1 mm) as required for a particular procedure on a patient or medical experiment, for example.

Figure 3:
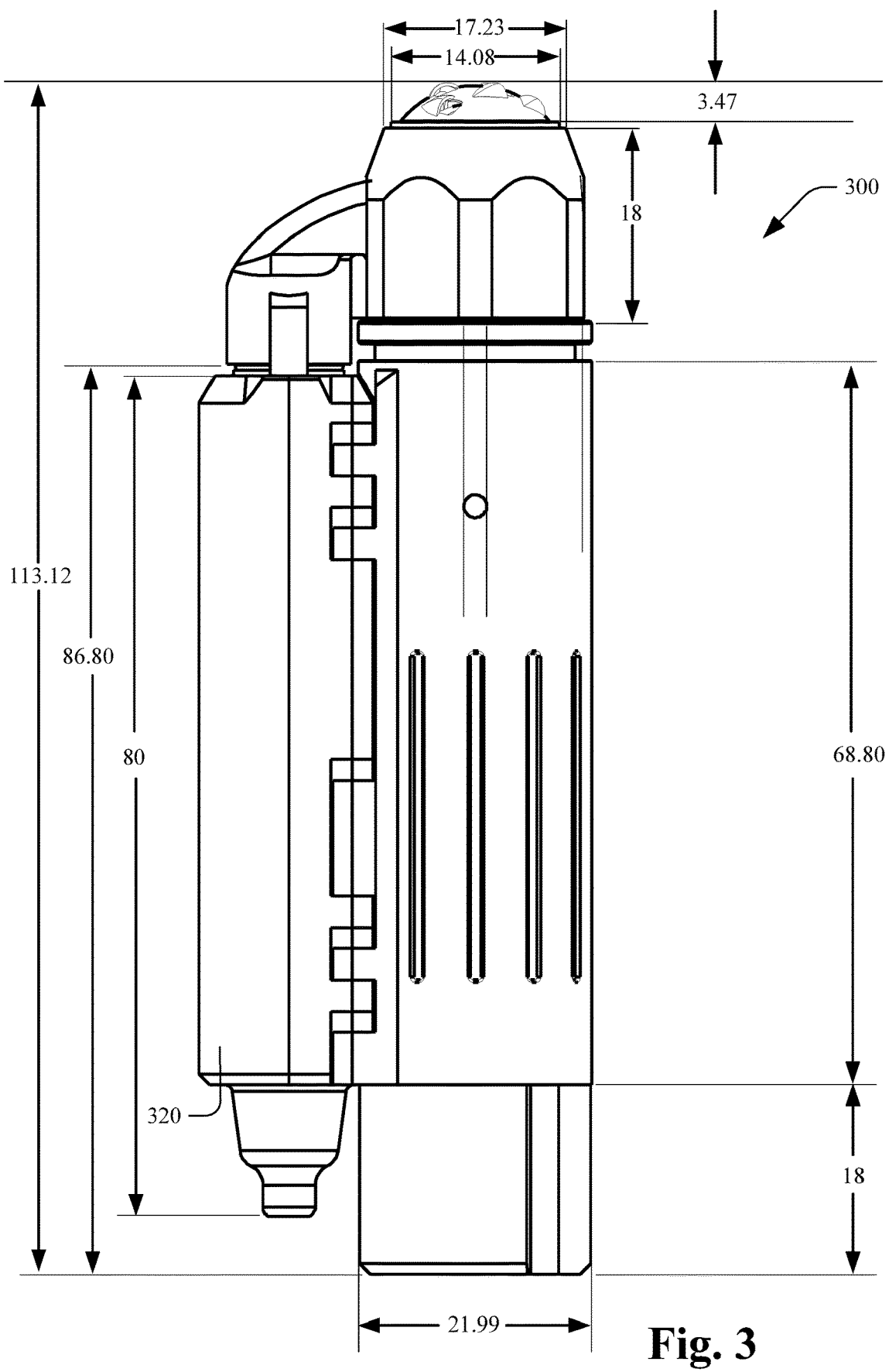
FIG. 3 illustrates a side view of a harvesting unit, in accordance with a particular aspect of the subject innovation.

FIG. 3 illustrates examples of dimensions in mm associated with a side view of a mobile hand held harvesting unit. In this particular aspect, the harvesting unit 300 employs a vacuum chamber 320 that supplies a suction mechanism that intakes the cartilage into the unit 300, via a differential pressure during operation. Such suction mechanism can further be facilitated in a scenario wherein the scooper component employs a rotational movement when accumulating the cartilage from the subject—hence increasing the differential pressure between the vacuum chamber and other parts of the harvesting unit (e.g., the scooper component). Subsequently, the cartilage can be drawn into (e.g., sucked into) the harvesting unit 300 and accumulated therein. To this end and the corresponding accumulation within the vacuum chamber 320 can be further facilitated via employing a porous collecting chamber (not shown). Such porous collecting chamber can function as a packaging for the accumulated cartridge. For example, from such porous collecting chamber, water an air can be ejected, hence creating a reservoir for the accumulated cartridge, whereby the porous collecting chamber can be removably detached from the vacuum chamber 320.

It is to be appreciated that employing a vacuum chamber 320 for accumulating the cartilage, and an access thereto via a porous collecting chamber(s) relates to a particular aspect of the subject disclosure. As such, other access mechanism are well within the realm of the subject innovation. For example, and as described infra with reference to FIGS. 4-7, the harvesting unit can be characterized a disposable unit that enables access to the cartilage by opening the harvesting unit or a breakage thereof, and hence exposing the cartilage accumulated therein.

Figure 4:
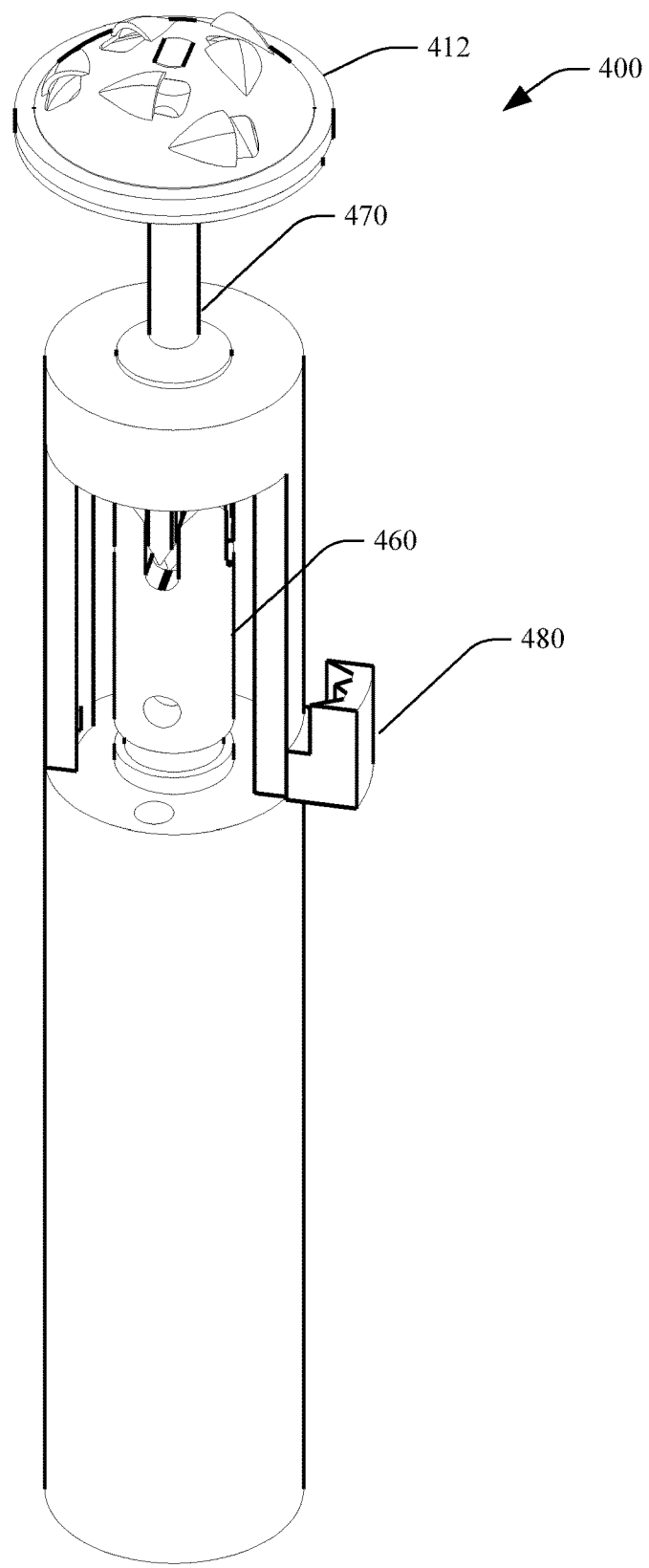
FIG. 4 illustrates a perspective for a harvesting unit that is disposable according to a further aspect of the subject innovation.
Figure 5:
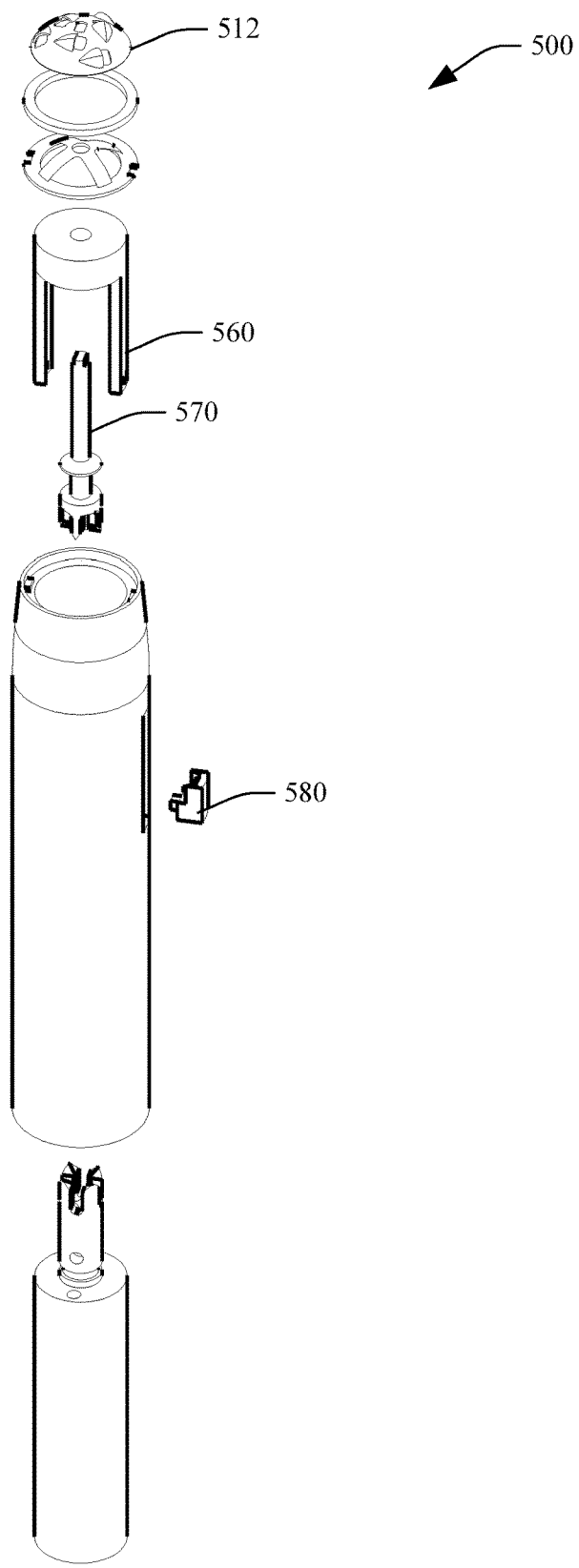
FIG. 5 illustrates a further perspective of exemplary parts for a disposable harvesting unit in accordance with a particular aspect of the subject innovation.

FIGS. 4-7 illustrate additional aspects of the subject disclosure, wherein the harvesting unit is designed for being thrown away after being used on a patient. Hence, by dismantling the harvesting unit, a supply of cartilage gathered and stored therein becomes readily available to an operator thereof. In one particular aspect, the accumulated cartilage can be released by employing a reciprocating element such as a pushout piston. FIG. 4 and FIG. 5 illustrate perspectives view of a disposable harvesting unit 400, 500 that employs a piston 460, 560, to enable access to the cartridge accumulated within the harvesting unit 400, 500. As illustrated the particular harvesting unit 400, 500 as depicted in FIG. 4 & FIG. 5 does not employ a vacuum chamber, nor a grinder shell for further grinding the cartilage on its way to the vacuum chamber. Nonetheless, introducing additional cutting/dicing/grinding aspects at various stages of harvesting the cartilage are well within the realm of the subject disclosure. Moreover, various biasing elements such as a loaded spring can facilitate operation of the reciprocating element or pushout piston, for example.

To this end, the piston 460, 560 can be operationally connected to a shaft 470, 570—whereby upon a user's pressing and sliding a push button 480, 580, the cartilage that is accumulated within the disposable harvesting unit 400, 500 is exposed, such as by dismantling or breaking the disposable harvesting unit 400, 500. In one aspect, a space between the shaver component 412, 512 and the piston 460, 560 can house the cartilage that is harvested by the harvesting unit 400, 500; and hence enables user access via operation of the push button 480, 580. To this end, the push button 480, 580 that is devised within the disposable harvesting unit 400, 500 can function as a trigger that breaks-up the disposable harvesting unit 400, 500, so that that the cartilage collected therein can be removed, for further processing—(such as being dispensed as a filler material and used in cosmetic operations.)

As explained earlier, the cartilage collected via the harvesting unit 400, 500 typically characterizes a size and density of cartilage, which when injected into to the imperfection space or volume of the patient, can fill it up without substantially shrinking in due time (e.g., the cartilage is not being absorbed within days to several decades after cosmetic treatment.) To this end, the cartilage collected by the harvesting unit 400, 500 can include a matrix of cells that have not been substantially damaged, such as the cells bursting because of the slicing, grinding and cutting operation to an extent that they are absorbed by the patient body—hence, defeating the purpose of the filler material. Accordingly, the cartilage collected by the harvesting unit 400, 500, contains substantially live cells after being sliced and diced, whereby cells associated with the cartilage are not substantially affected by these separation/division operations (e.g., substantially minimizing a surface contact area between the cartilage and cutting elements, to mitigate a burst of live cells.)

Figure 6:
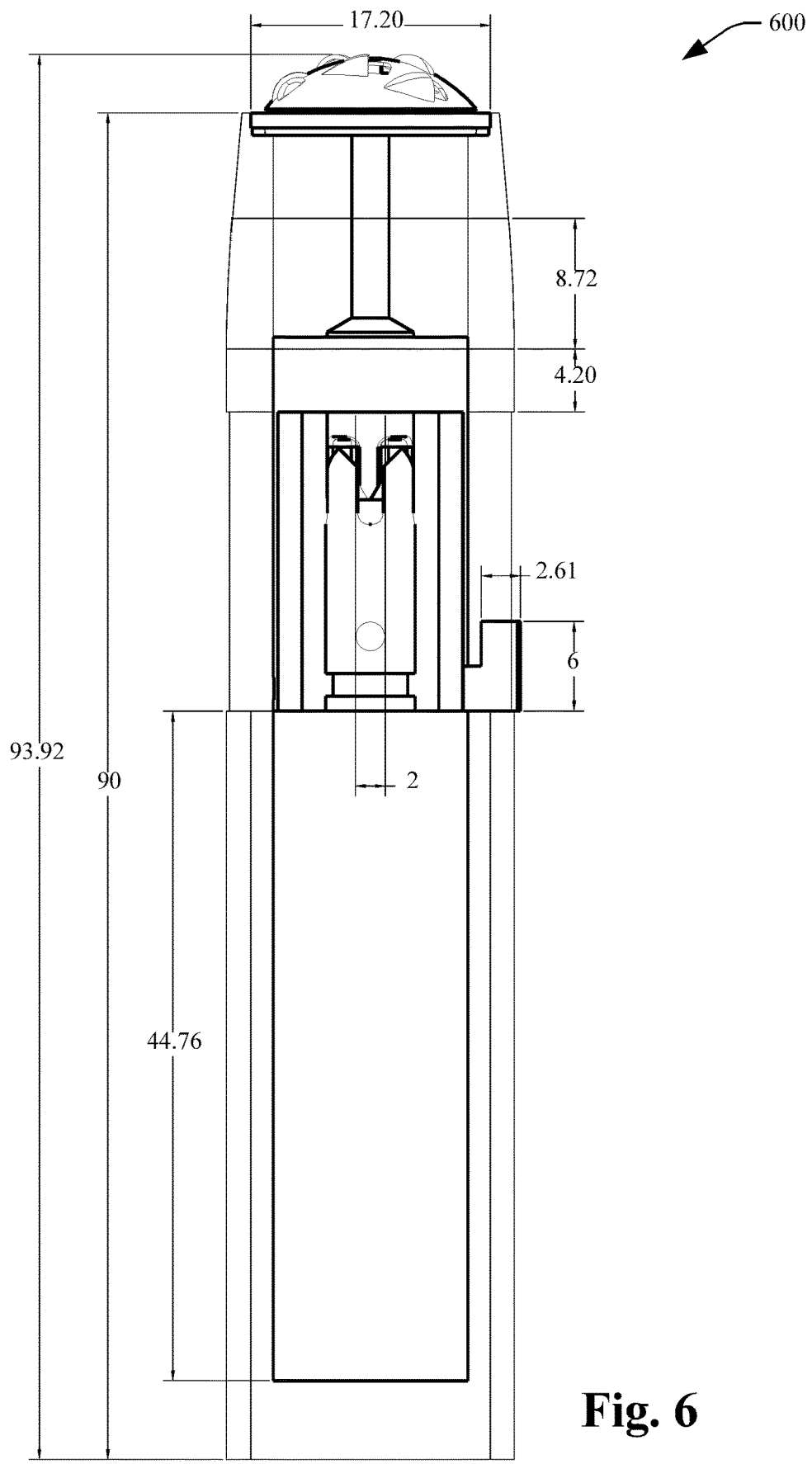
FIG. 6 illustrates a side view of a particular disposable harvesting unit according to a further aspect of the subject innovation.

FIG. 6 illustrates a particular side view of a disposable harvesting unit 600 that has been described above with reference to FIG. 4 & FIG. 5—wherein the dimensions are in mm. It is to be appreciated that such side view is exemplary in nature, and other sizes are well within the realm of the subject innovation. The disposable harvesting unit 600 can employ a piston arrangement, as described above.

Figure 7:
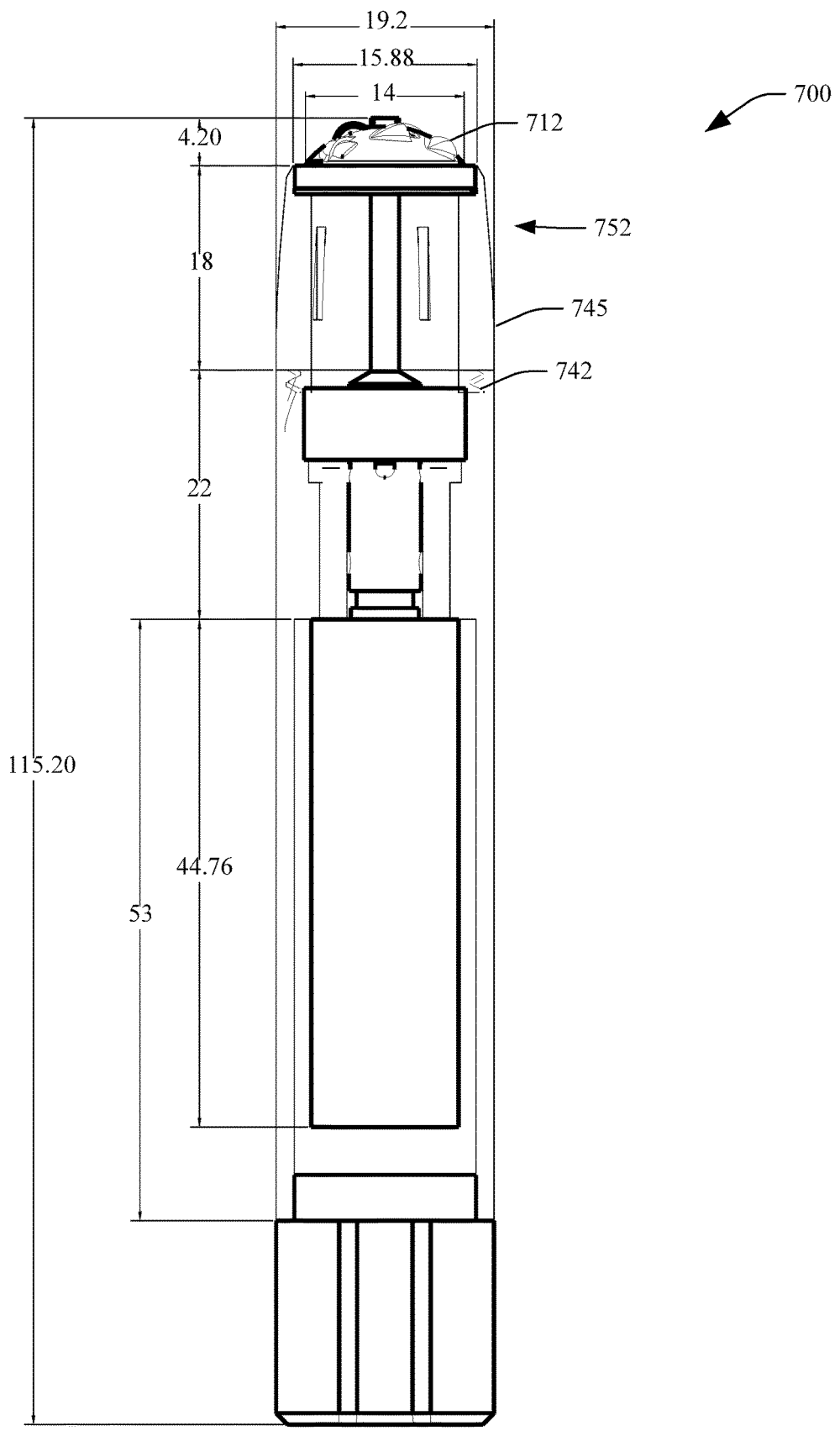
FIG. 7 illustrates another side view of a disposable harvesting unit in accordance with another aspect of the subject innovation.

FIG. 7 illustrates a particular harvesting unit 700 according to a further aspect of the subject disclosure that does not employ a piston element, for accessing the cartilage harvested. As illustrated, the harvesting unit 700 represents a disposable unit that enables access to the harvested cartilage—via a cap screw 745. The dimensions illustrated are exemplary in nature and are depicted in mm units.

According to one aspect, the cap screw 745 can function as a fastener having a helical ridge external thread that joins with a corresponding internal thread 742. For example, a clockwise rotation right hand thread engagement can be employed for attaching the cap screw 745 to the internal thread 742. Moreover, the disposable harvesting unit 700 can employ blades as part of its cutter component that remain parallel to base of the shaver component 712. The shaver component 712 can be part of the scooper component 752, as described in detail earlier, wherein the scooper component 752 can acquire or accumulate the cartilage. Subsequently, such cartilage so accumulated can be further divided into a plurality of pieces via a cutter component, for a reduction of size thereof.

In this regard, the scooper component 752 can substantially function as a collecting mechanism that gathers cartilage from the patient (e.g., by direct contact with the patient's body tissues) for subsequent processing—as opposed to—merely shaping such cartilage on body of the patient, to fashion a specific configuration.

It is to be appreciated that even though the scooper component 752 is described primarily in context of a rotational shaver component 712 and shaving operation other mechanisms of accumulation. Such mechanisms for detaching the cartilage from body of a patient can include: punching; piercing; extracting or a combination thereof when gathering or accumulating the cartilage and a subsequent processing thereof, for example. To this end, the amount of energy induced by the scooper component 752 onto the cartilage can be adjusted by factors such as hardness of the scooper component, speed of operation, grip force of the operator, and the like; as to reach a predetermined threshold for shaving or peeling or accumulating the cartilage.

FIG. 8 illustrates a schematic block diagram 800 of operation for a particular harvesting unit 862 that employs a vacuum chamber 869 having a porous collecting chamber 868, in accordance with a particular aspect of the subject innovation. The harvesting unit 862 can be operated by a power supply 867 that represents a battery. To this end, the harvesting unit 862 can be mobile and untethered for a free movement by operator thereof at various tilt angles that the harvesting unit is hand-held. Moreover, the scooper component 863 can function as a collecting mechanism that gathers cartilage from the patient by direct contact with the patient's body tissues, and further includes a shaver component 861.

The shaver component 861 can remove cartilage form body tissue of a patient 875 when it becomes in contact therewith. In this regard, the cutter component 864 can subsequently slice, dice, or grind the cartilage based on predetermined criteria. Such predetermined criteria can relate to extracellular matrix of the cartilage and based on subsequent processing requirements thereof, such as, dimensions of the cartilage, rate for division of chondrocyte cells, compressive or tensile strength, shear loading, viscoelastic properties, frictional characteristics, diffusion properties, and the like.

The harvesting unit 862 can include a vacuum chamber 869. Within the vacuum chamber 869 the cartilage can be accumulated in the porous collecting chamber 868, whereby water an air is ejected from such porous collecting chamber; hence leaving the cartilage therein. Stated differently, the porous collecting chamber 868 can function as a housing for removably attachable/detachable cartridges 891, 892, 893 (1 thru n, n being an integer). It is to be appreciated that various pumps and duct systems can also be employed that conduct lubricants (e.g., sterile water, normal saline and in general any type of lubricant that does not adversely affect the cartilage) into various portions of the harvesting unit—whereby cartilage can be separated from the lubricant via a filtering mechanism, for example.

As illustrated in FIG. 8, the processor 866 can facilitate operation of the harvesting unit 862 and further be part of an intelligent device, which has ability to sense or display information, or convert analog information into digital, or perform mathematical manipulation of digital data, or interpret the result of mathematical manipulation, or make decisions based on the information. As such, the processor 866 can be part of a logic unit, a computer or any other intelligent device capable of making operational decisions about collecting cartilage and reducing its size based on information and data provided to it.

As further illustrated in FIG. 8, a memory 877 is being coupled to the processor 866 as part of the harvesting unit 862. The memory 877 can store program code executed by the processor 866 for carrying out operating functions of the harvesting unit 862 as described herein. The memory 877 can include read only memory (ROM) and random access memory (RAM). The ROM contains among other code the Basic Input-Output System (BIOS), which controls the basic hardware operations of the harvesting unit 862. The RAM is the main memory into which the operating system and application programs are loaded. The memory 877 can also serve as a storage medium for temporarily storing information such as speed of the electro motor, characteristics of the cartilage the harvesting unit contacts or is being accumulated therein (e.g., density, hardness of the cartilage, space available in the porous collecting chamber 868, operating temperature tables, allowable temperature, required properties of the cartilage) and other data employed in carrying out the subject innovation. To this end and based on the data provided, the processor 866 can make decisions about operations of the harvesting unit 862, such as: speed of the electromotor 879 to control flow of the cartilage from the shaver component 861 to the cutter component 864; speed which the cartilage should be taken into the vacuum chamber 869; the space available therein—such as identifying whether any cartridge 891, 892, 893 is available for filling with cartilage, for example.

Figure 9:
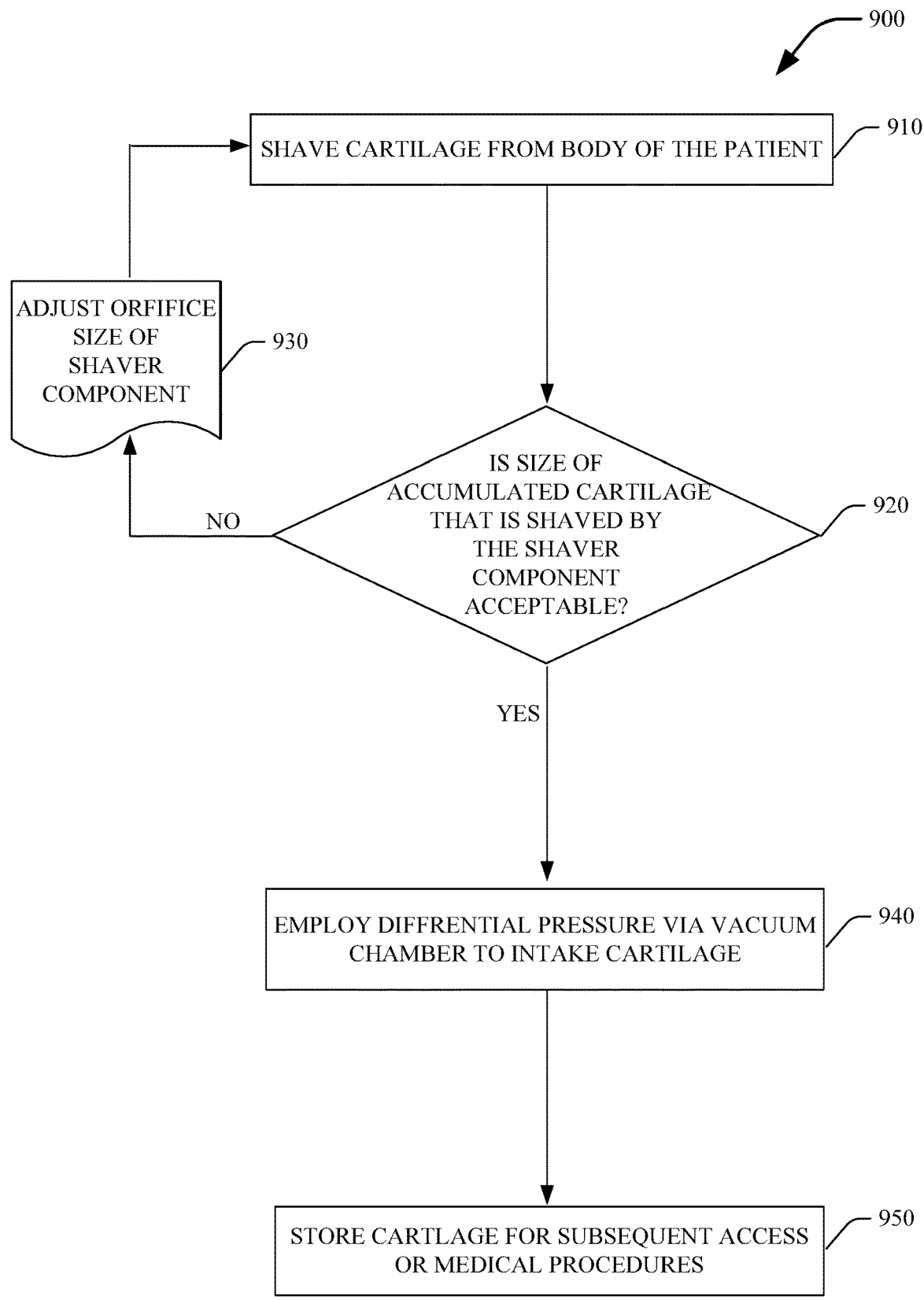
FIG. 9 illustrates an exemplary methodology about operation of the harvesting unit according to a further aspect of the subject innovation.

FIG. 9 illustrates a related methodology 900 of harvesting cartilage from a body of a subject, such as a patient in an automatic manner and via an electrically powered unit. While this exemplary method is illustrated and described herein as a series of blocks representative of various events and/or acts, the subject innovation is not limited by the illustrated ordering of such blocks. For instance, some acts or events may occur in different orders and/or concurrently with other acts or events, apart from the ordering illustrated herein, in accordance with the invention. In addition, not all illustrated blocks, events or acts, may be required to implement a methodology in accordance with the subject innovation. Moreover, it will be appreciated that the exemplary method and other methods according to the subject disclosure may be implemented in association with the method illustrated and described herein, as well as in association with other systems and apparatus not illustrated or described.

As illustrated, FIG. 9 is primarily described in conjunction with shaving the cartilage from the subject, and an accumulation thereof within the harvesting unit. Moreover, the methodology 900 additionally enables an adjustment of size (e.g., on-the-fly) for cartilage that is accumulated by the harvesting unit.

Initially and at 910, the cartilage can be directly shaved via a shaving operation that employs protrusions that engage body tissue of a patient. Such protrusions can include orifices that enable the cartilage to enter the harvesting unit. Subsequently, and at 920 a determination can be performed for evaluating size of the cartilage thus accumulated. For example, different filler material arising from different cartilage grafting can exhibit different size requirements, such as for density, injection characteristics, and the like.

To this end and if size of the cartilage is deemed unacceptable at act 920, the methodology 900 proceeds to act 930, whereby the harvesting unit receives replacement of its shaver component that has a different size, such as by adjusting the orifice size to a desired size. In a related aspect, such change of the orifice size can occur on-the-fly, and while an operator of the harvesting unit (e.g., a surgeon) is actually employing the harvesting unit.

In this regard and as explained earlier, an inner shell membrane can be positioned underneath the scooper component (e.g., covered thereby), such that a swivel motion of the inner shell membrane relative to the scooper component can partially block an orifice size associated therewith. A surface area of the orifice thus blocked, can subsequently affect the size of cartilage stripes that are shaved and accumulated by the harvesting unit.

On the other hand, if size of the cartilage accumulated is deemed acceptable at act 920, then the methodology 900 can proceed to act 940, wherein a differential pressure via a vacuum chamber can be applied to intake the cartilage within the harvesting unit. Such suction mechanism can further be facilitated in a scenario whereby the scooper component employs a shaver component having rotational movement when accumulating the cartilage from the patient; hence increasing the differential pressure between the vacuum chamber relative to other parts of the harvesting unit (e.g., the scooper component). Subsequently and at 950, the cartilage can then be stored in the harvesting unit for subsequent access. Such subsequent access can pertain to employing the cartilage that has been sliced or grinded for: creating additional cartilage cellular structure; which is injected into tissue of a patient requiring additional cartilage, for example.

Figure 10:
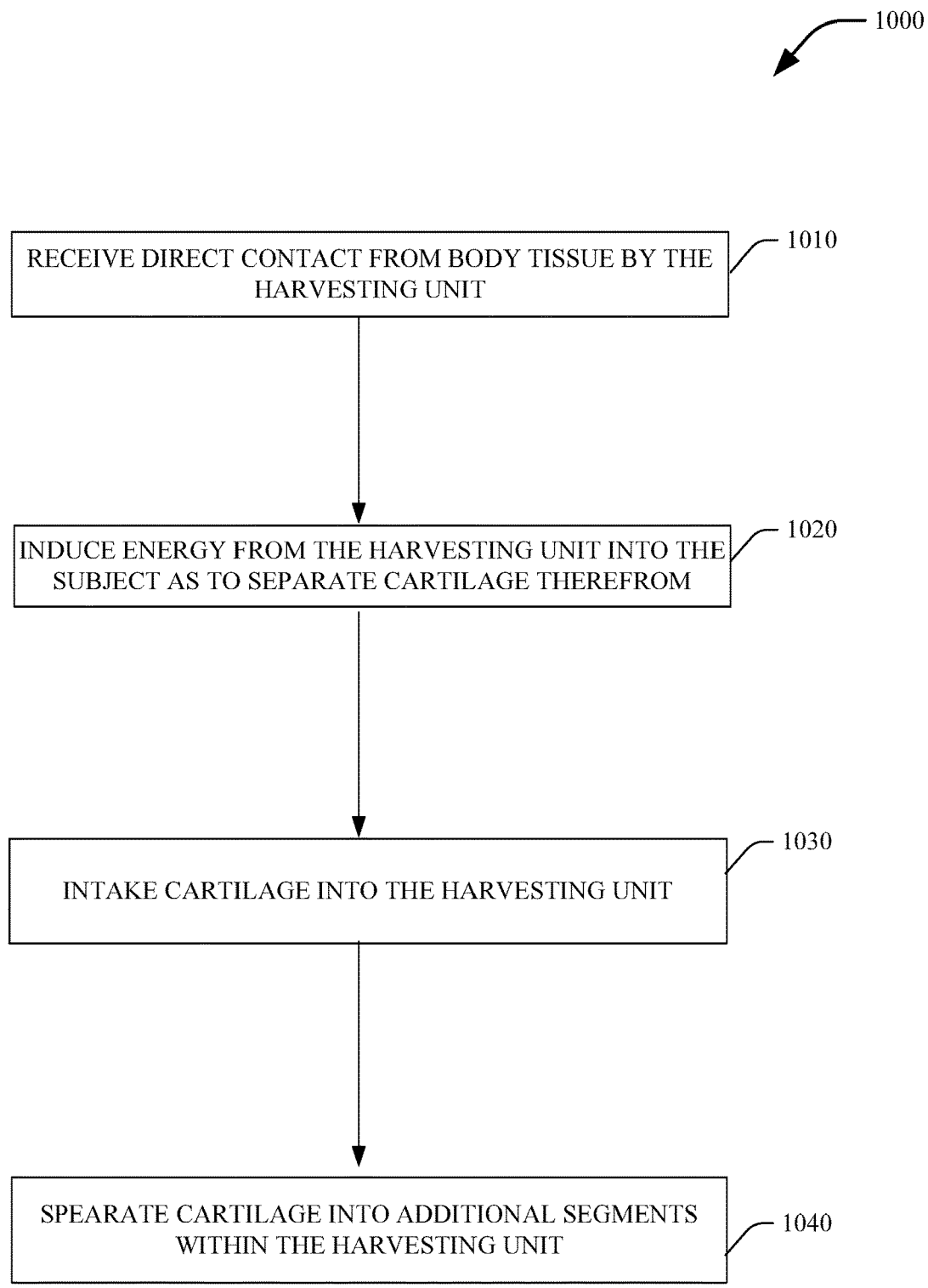
FIG. 10 illustrates a further methodology regarding operation of the harvesting unit according to a particular aspect of the subject innovation.

FIG. 10 illustrates a further methodology 1000 according to a particular aspect of the subject disclosure. Initially and at 1010 the harvesting unit receives a direct contact from the subject in form of a physical touching of body tissues, whereby cartilage can be collected therefrom. Subsequently and at 1020, an amount of energy sufficient to detach the cartilage from the subject can be induced from the harvesting unit into the subject. Such amount of energy can represent an amount of predetermined energy that remains sufficient to detach the cartilage from the subject, for example. In this regard, the amount of predetermined energy can be a function of specifications of the harvesting unit, such as speed of the electromotor, the characteristics of materials employed in building the harvesting unit (e.g., hardness of the shaver, an energy dissipation rate thereof, its brittleness, density, mass, and related physical or chemical properties that affect an ability to induce energy in a patient's body.) Likewise, such amount of predetermined energy that is required to detach cartilage from a patient can also be a function of characteristics of a patient's body, such as amount of fat or muscles in tissues of the patient, density/hardness/brittleness of the cartilage of the patient, gender/age of the patient, amount of mineral deposits in the body, family history, and the like. For example, an amount of predetermined energy required to detach a cartilage from one patient can be different from another patient—hence, in one particular example, user of the harvesting unit can adjust operations similar to a same manner that a dentist can adjust operations for different dental patients, for example. This can include changing the shaver component, adjusting speed of rotation of the electromotor, and the like, for example.

Next and at 1030 the harvesting unit intakes the cartilage from the subject that has been separated therefrom. At 1040, the cartilage thus received by the harvesting unit can further be separated into additional segments via a cutting or grinding operation or a combination thereof.

As such, the methodology 1000 enables partitioning of the cartilage and its division for size reduction via electric-powered-automated procedures, hence freeing a person from having to manually prepare or dice the cartilage for subsequent cosmetic methodologies. Hence, the methodology 1000 can enhance standards of cartilage collection and improve consistency of specifications that are associated with collecting and storing chondrocyte cells and their related extracellular matrix, for subsequent use (e.g., cartilage regeneration, creating cartilage dough for surgical procedures, cartilage injection, and the like).

For example, cartilage can be accumulated in form of a band or strip having a width within a range of 0.01 mm-1 mm, and a length within a range of 0.1 mm-10 mm. Such cartilage that is in shape of a stripe configuration can subsequently be diced into additional divide pieces (e.g., having a width within a range of 0.01 mm-0.4 mm, and a length within a range of 0.02 mm-4 mm). It is to be appreciated that such ranges are exemplary in nature and other dimensions can be obtained by varying a size of a bit of the shaver component and its associated cross cutter. In this regard, additional cutting or grinding stages for the methodology 900 can be employed that can further grind the cartilage into dough having a particle size that remains of sufficient size for enabling proper use (e.g., for various procedures that are employed for cartilage injection.)

Figure 11:
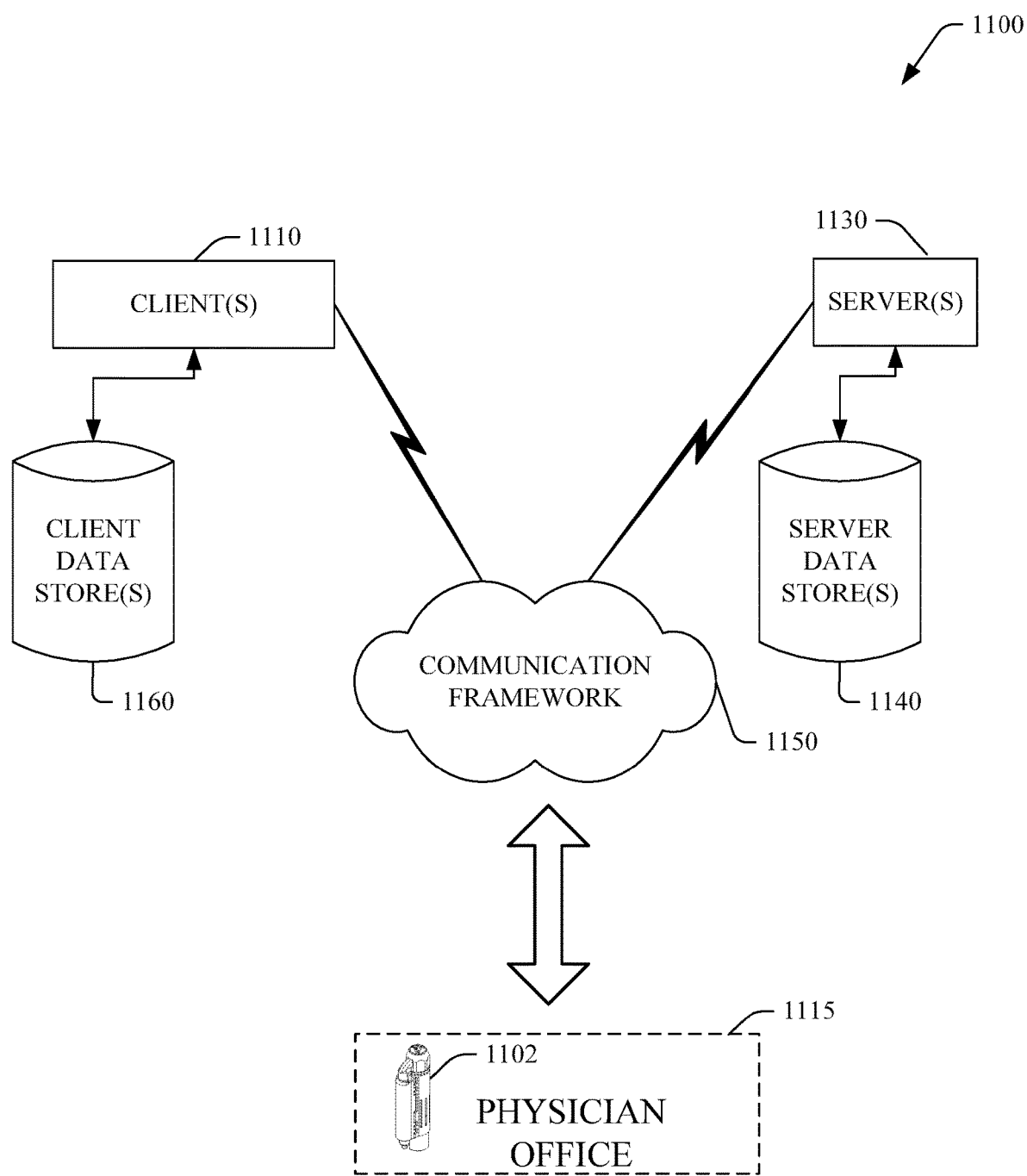
FIG. 11 illustrates an exemplary operating environment for implementing various aspects of the subject innovation.

FIG. 11 provides a context for the various setting such as a physician office 1115 or a hospital that the harvesting unit 1102 can be employed therein. Those skilled in the art will appreciate that the innovative methods can be practiced with other computer system configurations, including single-processor or multiprocessor computer systems, mini-computing devices, mainframe computers, as well as personal computers, hand-held computing devices (e.g., personal digital assistant (PDA), phone, watch . . . ), microprocessor-based or programmable consumer or industrial electronics, and the like. The illustrated aspects may also be practiced in distributed computing environments where tasks are performed by remote processing devices that are linked through a communications network. However, some, if not all aspects of the innovation can be practiced on stand-alone computers. In a distributed computing environment, program modules may be located in both local and remote memory storage devices.

The client(s) 1110 can be hardware and/or software (e.g., threads, processes, computing devices). The system 1100 also includes one or more server(s) 1130. The server(s) 1130 can also be hardware and/or software (e.g., threads, processes, computing devices). The servers 1130 can house threads to perform transformations by employing the components described herein, for example. One possible communication between the harvesting unit 1102 in the physician office 115, a client 1110 and a server 1130 may be in the form of a data packet adapted to be transmitted between two or more computer processes. The system 1100 includes a communication framework 1150 that can be employed to facilitate communications between the client(s) 1110 and the server(s) 1130 and the physician office 1115. The client(s) 1110 are operably connected to one or more client data store(s) 1160 that can be employed to store information local to the client(s) 1110. Similarly, the server(s) 1130 are operably connected to one or more server data store(s) 1140 that can be employed to store information local to the servers 1130.

Figure 12:
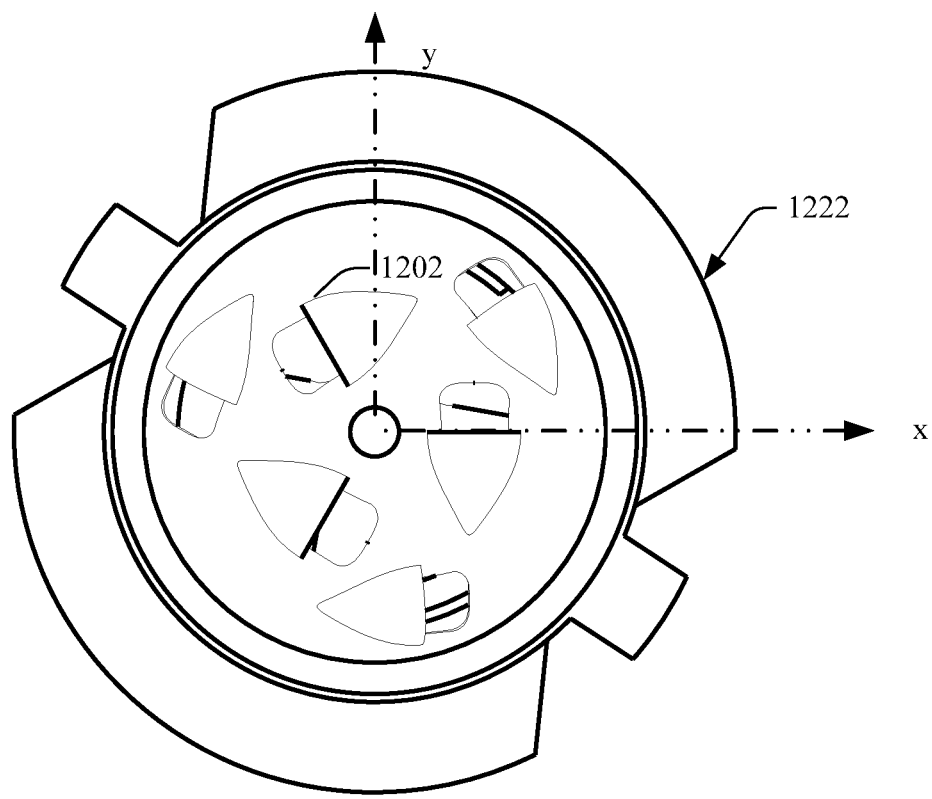
FIG. 12 illustrates various views of shaver components according to particular aspects of the subject innovation.
Figure 12:
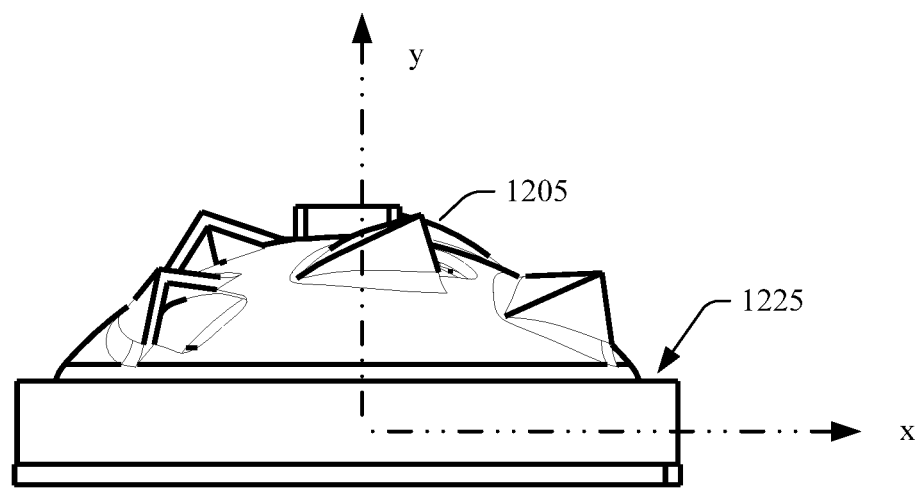

FIG. 12 illustrates various views of shaver components according to particular aspects of the subject disclosure. As illustrated various configurations for the protrusions 1202, 1205 can be employed, to shape the shaver component 1222, 1225 according to an aspect of the subject disclosure. For example, protrusion 1202 as depicted in the top view of shaver component 1222 can represent having a top surface in form of a dome. Likewise, protrusions 1205 with pointed edges can be employed as depicted in a side view of a different shaver 1225. Moreover, the protrusion 1202, 1205 can be symmetrical with respect to any of the horizontal axis (x), or with respect to the vertical axis (y) that pass through a center of the shaver component, or symmetrical with respect to both in a top view and/or a side view thereof, for example.

What has been described above includes various exemplary aspects. It is, of course, not possible to describe every conceivable combination of components or methodologies for purposes of describing these aspects, but one of ordinary skill in the art may recognize that many further combinations and permutations are possible. Accordingly, the aspects described herein are intended to embrace all such alterations, modifications and variations that fall within the spirit and scope of the appended claims.

Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A harvesting unit comprising:
   an electromotor operatively connected to a scooper component and a cutter component of the harvesting unit;
   the scooper component for an accumulation of cartilage from a body tissue upon a contact thereto;
   the cutter component for a separation of the cartilage into additional segments;
   the scooper component with an inner shell membrane having a swivel motion that adjusts an orifice of the harvesting unit, to change a size of the cartilage on-the-fly; and
   a duct system that conducts a fluid in the harvesting unit, the fluid for a lubrication of the cartilage and for an irrigation thereof.

2. The harvesting unit of claim 1 further comprising a power supply that provides a direct current to the electromotor.

3. The harvesting unit of claim 1, the scooper component further comprising a shaver component that shaves the body tissue for the accumulation.

4. The harvesting unit of claim 3, the shaver component with a plurality of protrusions that engage the body tissue.

5. The harvesting unit of claim 4, the shaver component with a rotational movement that rotates the plurality of protrusions.

6. The harvesting unit of claim 1 further comprising a vacuum chamber that facilitates the accumulation.

7. The harvesting unit of claim 6, the vacuum chamber further comprising a porous collecting chamber that houses cartridge(s) fillable by the cartilage.

8. The harvesting unit of claim 6 further comprising a pipe configuration that conveys the cartilage to the vacuum chamber.

9. The harvesting unit of claim 6 further comprising a lock mechanism that engages or disengages the vacuum chamber for an access to the accumulation.

10. The harvesting unit of claim 1 further comprising a piston that dismantles the harvesting unit, to access the accumulation.

11. The harvesting unit of claim 1 further comprising a processor that facilitates the accumulation.

12. A cartilage harvesting system comprising;
    means for inducing energy on a body tissue having cartilage for a separation of the cartilage therefrom;
    means for dividing the cartilage into additional portions without a manual dicing of the cartilage;
    means for changing a size of the cartilage on-the-fly; and
    means for conducting a fluid in the cartilage harvesting system for lubricating the cartilage to facilitate a flow thereof.

* * * * *